(12) United States Patent
Glick et al.

(10) Patent No.: US 10,849,739 B2
(45) Date of Patent: Dec. 1, 2020

(54) OPHTHALMOSURGICAL INJECTOR SYSTEM

(71) Applicant: Carl Zeiss Meditec AG, Jena (DE)

(72) Inventors: Robert Glick, Trabuco Canyon, CA (US); Vincent Sunio, Azusa, CA (US); Emma Meinke, Laguna Niguel, CA (US); Marco Müller, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 170 days.

(21) Appl. No.: 16/053,312

(22) Filed: Aug. 2, 2018

(65) Prior Publication Data

US 2020/0038171 A1 Feb. 6, 2020

(51) Int. Cl.
*A61F 2/16* (2006.01)
*A61M 5/315* (2006.01)

(52) U.S. Cl.
CPC ............ *A61F 2/167* (2013.01); *A61F 2/1678* (2013.01); *A61M 5/31505* (2013.01); *A61F 2002/1683* (2013.01); *A61F 2230/0013* (2013.01); *A61L 2430/16* (2013.01)

(58) Field of Classification Search
CPC ............ A61F 2/1662; A61F 2230/0013; A61F 2002/1683; A61F 2/1672; A61F 2/167; A61F 2/1678; A61F 2/1675; A61F 2/1664; A61F 2002/1682; A61M 5/31505
See application file for complete search history.

(56) References Cited

U.S. PATENT DOCUMENTS

| | | | | |
|---|---|---|---|---|
| 5,190,552 A | * | 3/1993 | Kelman | A61F 2/167 606/107 |
| 2011/0082463 A1 | * | 4/2011 | Inoue | A61F 2/1678 606/107 |
| 2014/0066946 A1 | * | 3/2014 | Aguilera | A61F 2/1662 606/107 |
| 2016/0015562 A1 | * | 1/2016 | Nagasaka | A61F 2/167 606/107 |
| 2016/0270907 A1 | * | 9/2016 | Attinger | A61F 2/167 |
| 2017/0172727 A1 | * | 6/2017 | Kanner | A61F 2/167 |

* cited by examiner

*Primary Examiner* — Katrina M Stransky
*Assistant Examiner* — Raihan R Khandker
(74) *Attorney, Agent, or Firm* — Falk Ewers; Ewers IP Law PLLC

(57) ABSTRACT

An ophthalmosurgical injector system includes an injector, which has a handpiece, a plunger and a dispensing device; an intraocular lens, which has an optic body, a C-shaped first haptic arm protruding from the optic body and a C-shaped second haptic arm protruding from the optic body; a cartridge, in which the intraocular lens is received, wherein the cartridge is inserted in the injector; and an actuation element, which has a contact surface, and a locking element, with which a position of the plunger relative to the handpiece or to the cartridge can be locked. The plunger can be locked in a first position, in which the intraocular lens is held in the cartridge in a compressed and pretensioned state in which an outer distance from the first haptic arm to the second haptic arm is greater than 8 mm and less than 11 mm.

7 Claims, 4 Drawing Sheets

OPHTHALMOSURGICAL INJECTOR SYSTEM

TECHNICAL FIELD

The disclosure relates to an ophthalmosurgical injector system, which has an injector, an intraocular lens, a cartridge, an actuation element, and a locking element.

BACKGROUND

In clouding of the lens of the human eye, referred to in medicine as cataract, it may be medically necessary to remove the clouded lens from the capsular bag. A method commonly used for this purpose is phacoemulsification of the lens, in which the clouded lens of a patient is emulsified into small particles by means of ultrasound and then aspirated. The surgeon subsequently inserts an artificial intraocular lens into the then lens-free capsular bag.

For this purpose, a surgeon can use an injector system, which has an injector. The injector has a handpiece, and a plunger which is guided in the handpiece and is longitudinally movable therein. In addition, the injector has an intraocular lens with an optic body. The intraocular lens can have two C-shaped haptic arms which protrude from the optic body and are arranged lying opposite each other, namely a first haptic arm and a second haptic arm. The haptic arms serve to come into contact with the inner wall of the capsular bag and to orient the optic body centrally within the capsular bag, such that better vision can be restored to the patient.

The injector system moreover has a cartridge, in which the intraocular lens is received, wherein the cartridge is insertable into the injector. In addition to the handpiece and the plunger, the injector has a dispensing device, wherein the dispensing device has an inlet opening at the proximal end and an outlet opening at the distal end. By means of a forward movement of the plunger, the intraocular lens can be conveyed through the cartridge and from there through the dispensing device in the direction of the outlet opening. During the operation, the surgeon uses the injector by pushing the outlet opening of the injector through the cornea of the eye as far as the capsular bag. Then, with an increasing forward movement of the plunger, the surgeon ensures that the intraocular lens is inserted through the dispensing device and from there into the capsular bag. The intraocular lens unfolds in the capsular bag in such a way that the haptic arms come to bear on the inner wall of the capsular bag and, in this way, the optic body is oriented centrally within the capsular bag.

The intraocular lens is initially in an untensioned state in the cartridge. The outer distance from the first haptic arm to the other, second haptic arm or the outer diameter of the intraocular lens is 12 mm in the untensioned state. The intraocular lens can be folded or rolled in the cartridge, for example by pivoting two wing elements about a hinge of the cartridge. By movement of the plunger into the handpiece, the intraocular lens can then be shifted forward and thus inserted into the capsular bag. A disadvantage of this is that an intraocular lens folded in this way has a low inherent stability. When the intraocular lens folded in this way is inserted into the capsular bag, the haptic arms unfold relatively quickly in the capsular bag. In doing so, they can cause a yawing movement of the whole intraocular lens about its optical axis and/or a rotation movement of the intraocular lens about its longitudinal axis, such that the intraocular lens turns uncontrollably. It is then difficult for an operating surgeon to move the intraocular lens back to the desired position. If this is not achieved in full, there is the possibility of a patient not acquiring optimal vision.

SUMMARY

It is an object of the disclosure to make available an ophthalmosurgical injector system with which an intraocular lens, contained in the former, can be conveyed easily and safely through a dispensing device of the injector system, wherein the injector system is of a compact design, and a patient is afforded optimal vision after implantation of the intraocular lens with the injector system.

This object is achieved by an ophthalmosurgical injector system as disclosed herein.

The ophthalmosurgical injector system includes:
- an injector, which has a handpiece, a plunger and a dispensing device;
- an intraocular lens, which has an optic body, a C-shaped first haptic arm protruding from the optic body and a C-shaped second haptic arm protruding from the optic body;
- a cartridge, in which the intraocular lens is received, wherein the cartridge is inserted in the injector;
- an actuation element, which has a contact surface;
- a locking element, with which a position of the plunger relative to the handpiece or to the cartridge can be locked;

i) wherein the dispensing device has an inlet opening at the proximal end and an outlet opening at the distal end, wherein the intraocular lens, by a forward movement of the plunger, can be conveyed through the cartridge and then through the inlet opening to the outlet opening of the dispensing device, ii) wherein the plunger can be locked, by the locking element, in a first position, in which the intraocular lens is held in the cartridge in a compressed and pretensioned state in which an outer distance from the first haptic arm to the second haptic arm is greater than 8 mm and less than 11 mm, and iii) wherein a linear movement or pivoting movement of the actuation element brings the contact surface of the actuation element into engagement with the plunger in order to achieve a forward movement of the plunger by at least 2 mm to at most 4 mm to a second position, as a result of which a subregion of the first haptic arm and a subregion of the second haptic arm are placed above the optic body, wherein the plunger can be locked in the second position by the locking element.

In a first position of the plunger, in which the plunger is locked, the injector system according to the disclosure makes it possible for the intraocular lens to be pretensioned in the cartridge and stored in this state. Even after a very long storage time of the injector system, the haptic arms are only elastically deformed, not plastically deformed. With the injector system, it is additionally possible to more strongly compress the intraocular lens before the implantation, by placing the plunger in a second position. This can be done by a surgeon shortly before an operation.

In the second position, the haptic arms are arranged above the optic body. This second position is advantageous for folding or rolling up the intraocular lens by pivoting the wing elements of the cartridge such that the intraocular lens can be easily pushed into the dispensing device by a forward movement of the plunger. The use of the securing element ensures that the haptic arms are compressed for a predetermined path length of at least 2 mm to at most 4 mm. If this additional compression is applied only for a relatively short time, since the surgeon performs this compression just shortly before the operation, no plastic deformation occurs at a respective bending joint on the shaft of a haptic arm. A situation where the haptic arms are accidentally pushed beyond the predetermined path length, which could lead to a plastic deformation of the bending joint on the shaft of a haptic arm, can be avoided through use of the actuation element, since the haptic arms are compressed only for a predetermined path length of at least 2 mm to at most 4 mm. The outer distance between the haptic arms is relatively short in this state, such that the intraocular lens is present in a relatively compact form. During an implantation into a capsular bag, it is thus possible to avoid the intraocular lens twisting about its own longitudinal axis or about its optical axis, since the haptic arms do not deploy too early. Instead, the haptic arms initially deploy within the capsular bag, and it is only thereafter that the haptic arms move back completely to their original position, such that the patient is afforded optimal vision.

The locking element or locking mechanism is typically a mechanical latching element, for example a ratchet, which inhibits or blocks the plunger only in a rearward direction. The locking element can come into engagement only with the handpiece or only with the cartridge or in combination with the handpiece and with the cartridge. If the locking element connects the plunger to the cartridge, locking can take place in direct proximity to the intraocular lens. Thus, during what may be a long period of storage of the injector system, the intraocular lens can be pretensioned in a relatively secure and stable manner.

After the plunger has been position in the second position, the haptic arms are located above the optic body. However, there remains a still sufficiently large surface area of the optic body that is not covered by the haptic arms and that therefore cannot be damaged by the haptic arms in any way, for example by scratching.

A further advantage of the injector system is that, through use of the actuation element and an associated forward movement of the plunger by a predetermined length, there is no danger of the intraocular lens being conveyed too far into the dispensing device before folding. Instead, directly before the operation, the surgeon simply has to convey the plunger to the second position, introduce a viscoelastic into the cartridge and then move the wing arms toward each other in order to fold the intraocular lens. Alternatively, the viscoelastic can also be introduced after the intraocular lens has been folded. The surgeon can then immediately begin conveying the intraocular lens through the dispensing device. During this movement of the plunger, the force that has to be applied is relatively constant. The surgeon no longer has to apply the relatively low force for compressing the haptic arms, and therefore the surgeon no longer has to take into account a considerable difference between the forces that are to be applied during the movement of the plunger. Overall, this means that the intraocular lens can be easily and safely conveyed through the dispensing device of the injector system by the surgeon.

In addition, the injector system according to the disclosure allows the length of the injector to be kept shorter than before. The intraocular lens, which in the untensioned state has an outer distance of approximately 12 mm from the first haptic arm to the second haptic arm, is shorter in the compressed and pretensioned state. The injector system can thus be produced and supplied in a more compact form.

According to an exemplary embodiment of the disclosure, the cartridge has wing elements coupled to hinges, such that, in an opened position of the wing elements, the insertion of the intraocular lens into the cartridge is permitted and, by pivoting the wing elements to a closed position, the folding of the inserted intraocular lens is permitted. The pivoting of wing elements to a closed position can be performed very easily by a surgeon, and no forward movement of a plunger is needed to achieve folding of the intraocular lens.

The intraocular lens is typically made of a hydrophobic acrylic polymer. This permits compression, pretensioning and storage of the intraocular lens over several years, after which the intraocular lens, when inserted into a capsular bag, nevertheless is able to unfold completely into an untensioned state.

BRIEF DESCRIPTION OF THE DRAWINGS

The disclosure will now be described with reference to the drawings wherein.

iii)

DESCRIPTION OF EXEMPLARY EMBODIMENTS

Figure 1:
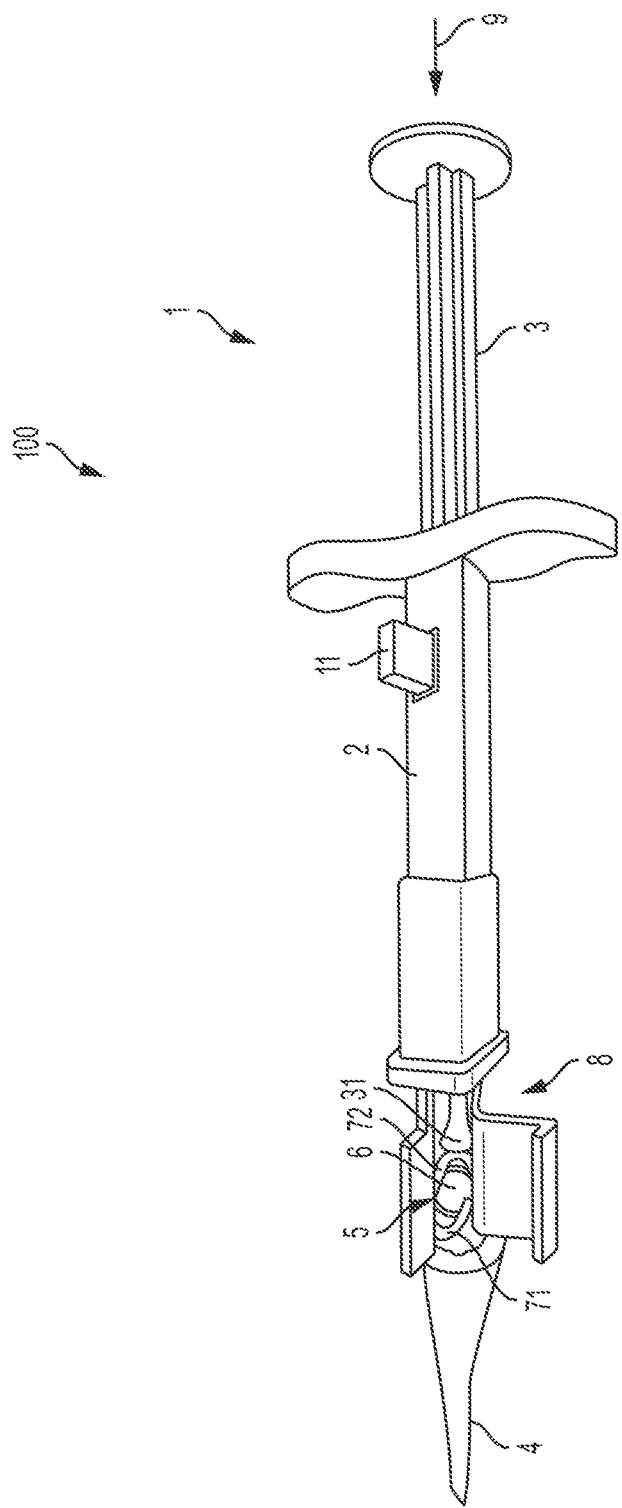
FIG. 1 shows a schematic illustration of an injector system according to the disclosure.

FIG. 1 shows a schematic illustration of an exemplary embodiment of an ophthalmosurgical injector system 100 according to the disclosure. The injector system 100 has an injector 1, which has a handpiece 2 and a plunger 3. In addition, the injector 1 has a dispensing device 4 through which an artificial intraocular lens 5 can be conveyed. The intraocular lens 5 has an optic body 6 and two C-shaped haptic arms 7, which protrude therefrom and are arranged lying opposite each other, namely a first haptic arm 71 and a second haptic arm 72 (see also FIG. 2). The intraocular lens 5 is inserted in a cartridge 8, which is positioned in the injector system 100 before the dispensing device 4. By means of a forward movement (see arrow 9), the plunger 3 guided in the handpiece 2 can have its distal end 31 come into contact with the second haptic arm 72, whereupon both haptic arms 72 and 71 bend in directions toward the optic body 6.

Figure 2:
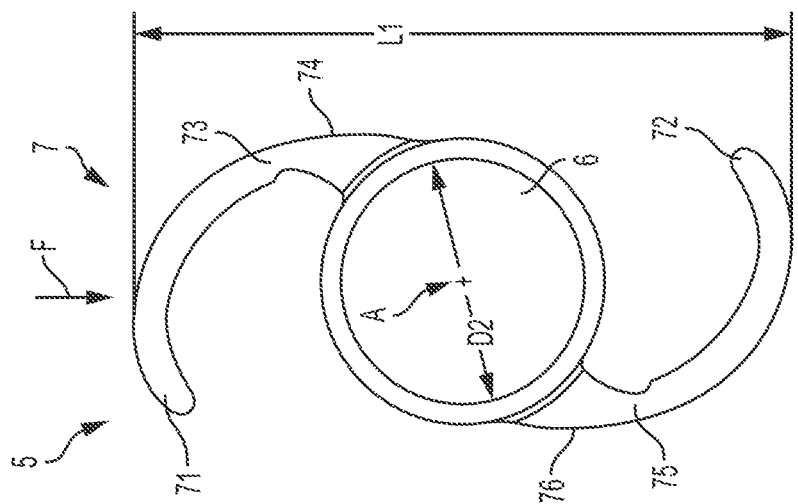
FIG. 2 shows a schematic illustration of an artificial intraocular lens in the untensioned state, in a plan view.

The intraocular lens 5 is in an untensioned state at the time of production, such that the outer distance from the first haptic arm 71 to the second haptic arm 72 has a length L1 (see FIG. 2). The length L1 can measure 12 mm. When the distal end 31 of the plunger 3 applies a force F to one of the haptic arms 71, 72 in a direction perpendicular to an optical axis A of the optic body 6, the first haptic arm 71 bends about a bending joint 73. The bending joint 73 is provided on a shaft 74 of the first haptic arm 71. Analogously to this, there is a second bending joint 75 on the second haptic arm 72, which second bending joint 75 is provided on a second shaft 76 of the second haptic arm 72. On account of the elasticity of the material of the intraocular lens, which is typically a hydrophobic acrylic polymer, such bending of the haptic arms can be permitted in the direction of the optic body 6.

Figure 3:
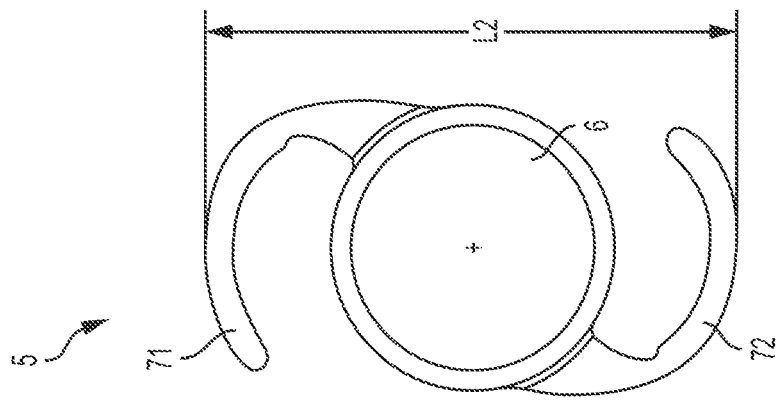
FIG. 3 shows a schematic illustration of the artificial intraocular lens in a first compressed state, in a plan view.

FIG. 3 shows the intraocular lens 5 in a first compressed state, when the plunger is located in the first position. The outer distance from the first haptic arm 71 to the second haptic arm 72 then measures L2, wherein L2 is less than L1. L2 is greater than 8 mm and less than 11 mm.

Figure 4:
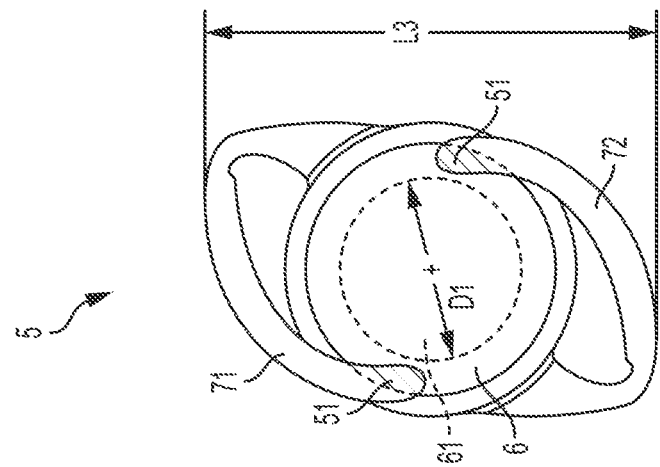
FIG. 4 shows a schematic illustration of the artificial intraocular lens in a second compressed state, in a plan view.

When the plunger is located in the second position, this leads to still greater compression of the intraocular lens 5, wherein a subregion 51 of each of the haptic arms 71, 72 lies on the optic body 6 and partially covers the latter there (see FIG. 4). The optic body 6 of the pretensioned intraocular lens 5 has, in a plan view, a circular surface area 61 not covered by the haptic arms 71, 72, which circular surface area 61 has a diameter D1 of typically at least 4.5 mm. The outer circumference of the circular surface area 61 is shown by a dotted line in FIG. 4. In this compressed state of the intraocular lens 5, the outer distance from the first haptic arm 71 to the opposite second haptic arm 72 has a length L3, which is shorter than the length L2 or L1. With a length L1 of 12 mm, such compression of the intraocular lens 5 leads to a length L3 of approximately 6 mm to 9 mm, typically 6 mm to less than 7.5 mm. The subregion 51 is a surface representing part of a circular ring which is formed between a ring with the external diameter D2 of the optic body 6 and a ring with the diameter D1 of the circular surface area 61 (see FIG. 2 and FIG. 4).

Figure 5:
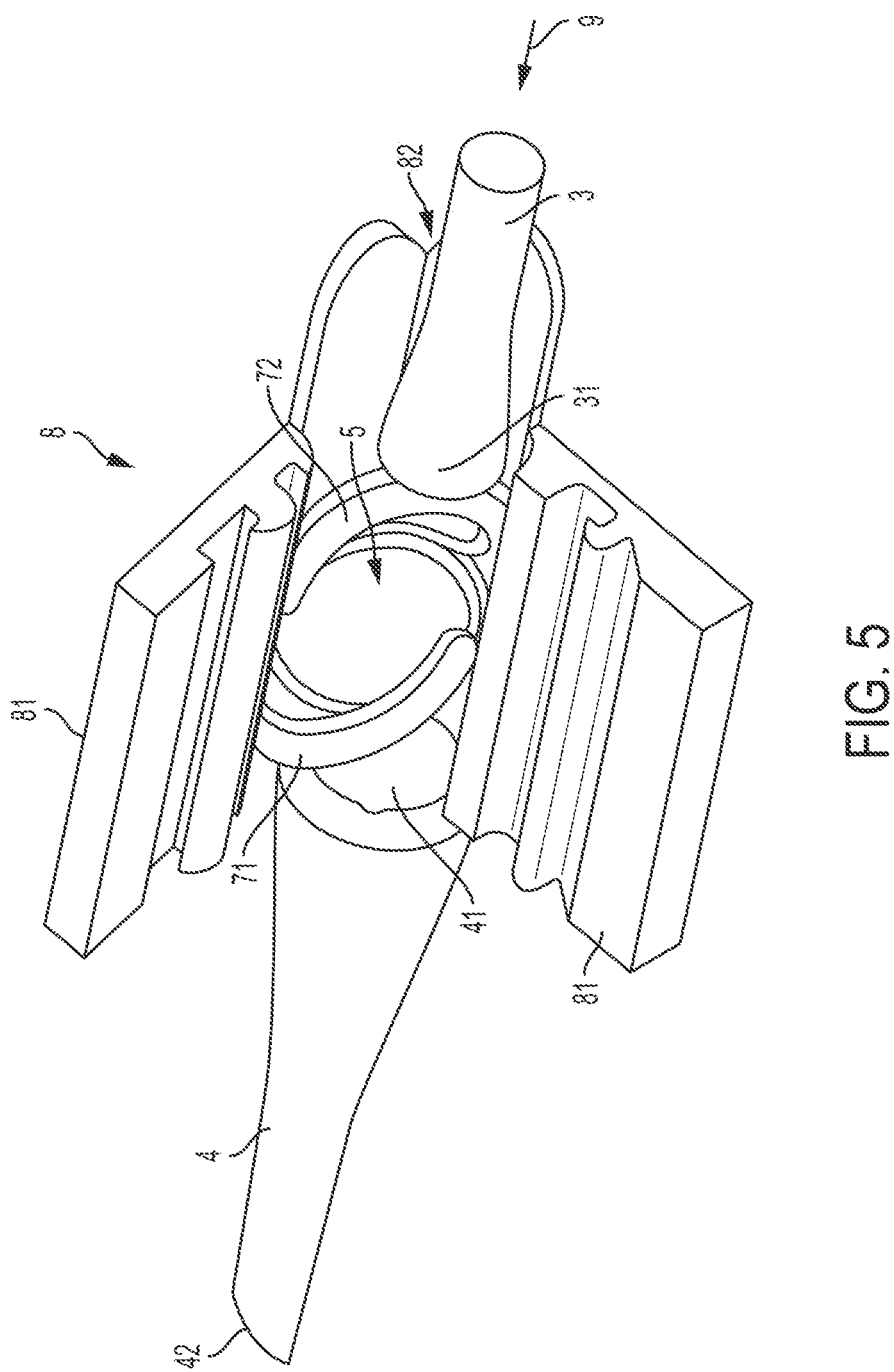
FIG. 5 shows a schematic perspective illustration of a cartridge with wing elements and an intraocular lens inserted into the cartridge and compressed; and vi)

FIG. 5 shows a perspective illustration of the intraocular lens 5 inserted in the cartridge 8 and compressed. The distal end 31 of the plunger 3 is in touching contact with the second haptic arm 72. The cartridge 8 has two wing elements 81, which are shown in an opened position in FIG. 5. By pivoting the wing elements 81 about an associated hinge 82, typically a film hinge, the intraocular lens 5 can be folded or rolled up, such that it can be pushed into an inlet opening 41 of the dispensing device 4. By continued movement of the plunger 3 in the direction of the arrow 9, the intraocular lens 5 emerges at the distal end of the dispensing device 4, at the outlet opening 42 of the latter, to be introduced into a capsular bag of an eye.

Figure 6:
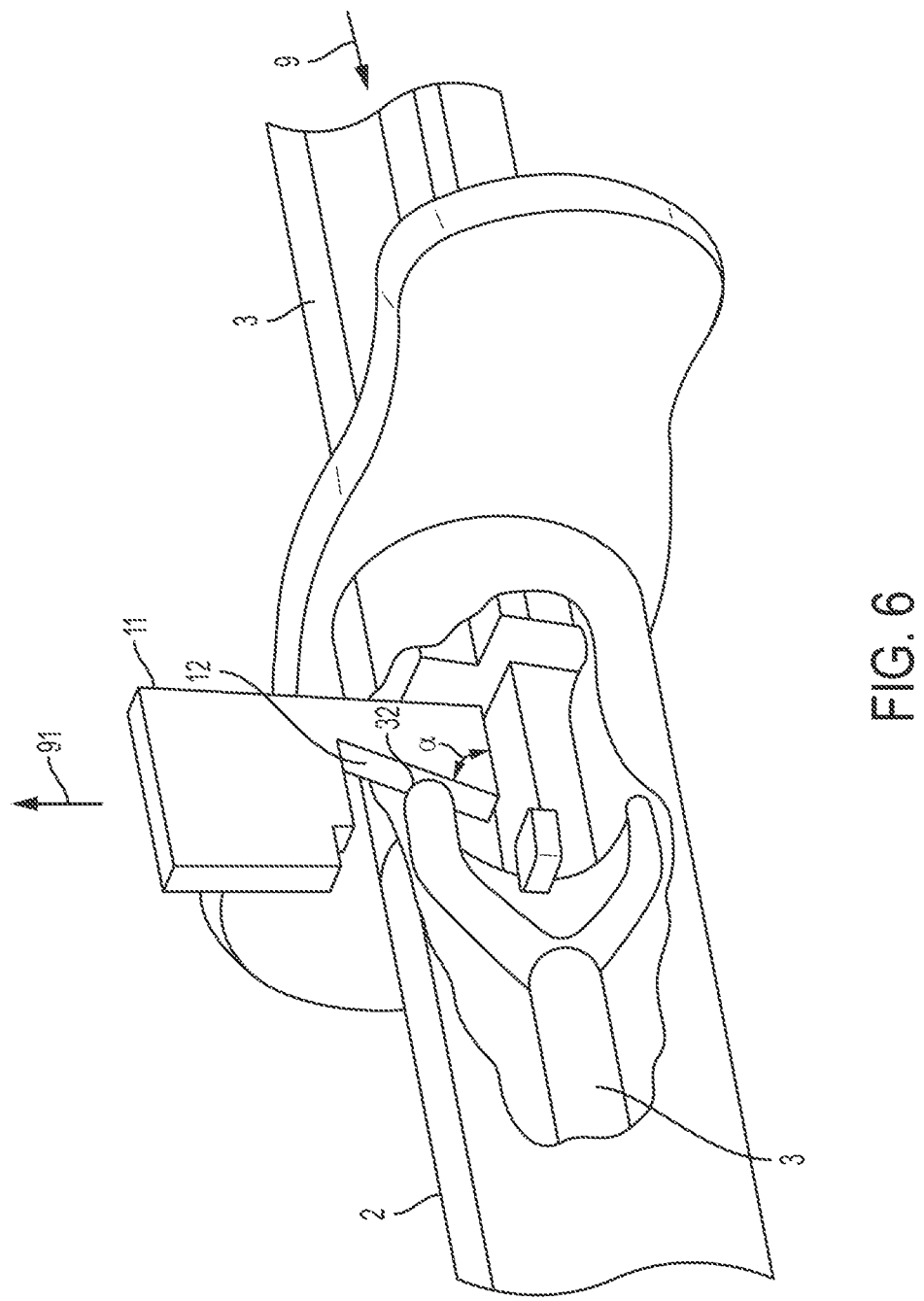
FIG. 6 shows a schematic perspective illustration of an actuation element, which is in engagement with the plunger of the injector system.

FIG. 6 shows a schematic perspective illustration of an actuation element 11, which is in engagement with the plunger 3. The actuation element 11 has a plane contact surface 12 which can be coupled with form-fit engagement to a corresponding contact surface 32 of the plunger 3. The contact surfaces 12 and 32 are typically resiliently pretensioned and provide the locking mechanism according to an exemplary embodiment of the disclosure. By a linear movement of the actuation element 11 in the direction of the arrow 91, which is typically perpendicular to the direction of the forward movement (see arrow 9), the plunger 3 is moved in the direction of the arrow 9 by the predetermined distance of at least 2 mm to at most 4 mm. The contact surface 12 is typically configured as a ramp, wherein an angle α between an inclination plane of the contact surface 12 and the longitudinal axis of the plunger 3 is greater than 45°. Instead of having a plane surface, the contact surface 12 can also be configured as a free-form surface or as a differently curved surface, provided that actuating the actuation element in a linear movement or pivoting movement leads to a displacement of the plunger by a predetermined distance of at least 2 mm and at most 4 mm.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

REFERENCE SIGNS 1 injector
2 handpiece
3 plunger
4 dispensing device
5 intraocular lens
6 optic body
7 haptic arms
8 cartridge
9 arrow for forward movement
11 actuation element
12 contact surface of the actuation element
31 distal end of the plunger
32 contact surface of the plunger
41 inlet opening of the dispensing device
42 outlet opening of the dispensing device
51 subregion of a haptic arm
61 circular surface area
71 first haptic arm
72 second haptic arm
73 bending joint on the first haptic arm
74 shaft of the first haptic arm
75 bending joint on the second haptic arm
76 shaft of the second haptic arm
81 wing element
82 hinge
91 pulling direction of the actuation element
100 injector system
A optical axis
D1 diameter of the circular surface area of the optic body not covered by haptic arms
D2 external diameter of the optic body

The invention claimed is:

1. An ophthalmosurgical injector system comprising:
an injector including a handpiece, a plunger, and a dispensing device;
an intraocular lens including an optic body, a C-shaped first haptic arm protruding from the optic body, and a C-shaped second haptic arm protruding from the optic body;
a cartridge configured to receive the intraocular lens, wherein the injector is configured to receive the cartridge;
an actuation element having a contact surface; and
a locking mechanism configured to lock a position of the plunger relative to the handpiece or to the cartridge;
wherein the dispensing device has an inlet opening at a proximal end and an outlet opening at a distal end,
wherein the plunger is configured to convey the intraocular lens through the cartridge and then from the inlet opening to the outlet opening of the dispensing device by a forward movement of the plunger, wherein the locking mechanism is configured to lock the plunger in a first position, in which the intraocular lens is held in the cartridge in a compressed and pretensioned state in which an outer distance from the first haptic arm to the second haptic arm is greater than 8 mm and less than 11 mm, wherein the actuation element is configured to bring the contact surface of the actuation element into engagement with the plunger by a linear movement of the actuation element to directly achieve a linear forward movement of the plunger by at least 2 mm to at most 4 mm to a second position, as a result of which a subregion of the first haptic arm and a subregion of the second haptic arm are placed above the optic body, and wherein the locking mechanism is configured to lock the plunger in the second position.

2. The ophthalmosurgical injector system as claimed in claim 1, wherein the linear movement is a pulling movement, and wherein the actuation element is configured to execute the forward movement of the plunger in response to the pulling movement perpendicular to a direction of the forward movement of the plunger.

3. The ophthalmosurgical injector system as claimed in claim 1, wherein the intraocular lens is made of a hydrophobic acrylic polymer.

4. An ophthalmosurgical injector system comprising:

an injector including a handpiece, a plunger, and a dispensing device;

an intraocular lens including an optic body, a C-shaped first haptic arm protruding from the optic body, and a C-shaped second haptic arm protruding from the optic body;

a cartridge configured to receive the intraocular lens, wherein the injector is configured to receive the cartridge;

an actuation element having a contact surface; and a locking mechanism configured to lock a position of the plunger relative to the handpiece or to the cartridge;

wherein the dispensing device has an inlet opening at a proximal end and an outlet opening at a distal end, wherein the plunger is configured to convey the intraocular lens through the cartridge and then from the inlet opening to the outlet opening of the dispensing device by a forward movement of the plunger, wherein the locking mechanism is configured to lock the plunger in a first position, in which the intraocular lens is held in the cartridge in a compressed and pretensioned state in which an outer distance from the first haptic arm to the second haptic arm is greater than 8 mm and less than 11 mm, wherein the actuation element is configured to bring the contact surface of the actuation element into engagement with the plunger by a pivoting movement of the actuation element to achieve a forward movement of the plunger by at least 2 mm to at most 4 mm to a second position, such that (i) a subregion of the first haptic arm and a subregion of the second haptic arm are placed above the optic body, (ii) the optic body, in a plan view, has a circular surface area not covered by the first haptic arm and the second haptic arm, and (iii) a diameter of the circular surface area not covered by the first haptic arm and the second haptic arm is at least 4.5 mm, and wherein the locking mechanism is configured to lock the plunger in the second position.

5. The ophthalmosurgical injector system as claimed in claim 4, wherein the intraocular lens is made of a hydrophobic acrylic polymer.

6. An ophthalmosurgical injector system comprising:

an injector including a handpiece, a plunger, and a dispensing device;

an intraocular lens including an optic body, a C-shaped first haptic arm protruding from the optic body, and a C-shaped second haptic arm protruding from the optic body;

a cartridge configured to receive the intraocular lens, wherein the injector is configured to receive the cartridge;

an actuation element having a contact surface; and a locking mechanism configured to lock a position of the plunger relative to the handpiece or to the cartridge;

wherein the dispensing device has an inlet opening at a proximal end and an outlet opening at a distal end, wherein the plunger is configured to convey the intraocular lens through the cartridge and then from the inlet opening to the outlet opening of the dispensing device by a forward movement of the plunger, wherein the locking mechanism is configured to lock the plunger in a first position, in which the intraocular lens is held in the cartridge in a compressed and pretensioned state in which an outer distance from the first haptic arm to the second haptic arm is greater than 8 mm and less than 11 mm, wherein the actuation element is configured to bring the contact surface of the actuation element into engagement with the plunger by a linear movement of the actuation element to achieve a forward movement of the plunger by at least 2 mm to at most 4 mm to a second position, such that (i) a subregion of the first haptic arm and a subregion of the second haptic arm are placed above the optic body, (ii) the optic body, in a plan view, has a circular surface area not covered by the first haptic arm and the second haptic arm, and (iii) a diameter of the circular surface area not covered by the first haptic arm and the second haptic arm is at least 4.5 mm, and wherein the locking mechanism is configured to lock the plunger in the second position.

7. The ophthalmosurgical injector system as claimed in claim 6, wherein the intraocular lens is made of a hydrophobic acrylic polymer.

* * * * *